United States Patent [19]

Overmyer

[11] Patent Number: 4,695,255

[45] Date of Patent: Sep. 22, 1987

[54] METHOD OF COOLING AND LUBRICATING HUMAN HARD TISSUE DURING POWER TOOL CUTTING

[76] Inventor: Thad J. Overmyer, 132 N. Second St., Danville, Ky. 40422

[21] Appl. No.: 866,928

[22] Filed: May 27, 1986

[51] Int. Cl.⁴ .............................................. A61C 5/00
[52] U.S. Cl. .................................................. 433/215
[58] Field of Search ...................... 433/215, 35, 87, 85, 433/84, 82, 80, 81

[56] References Cited

U.S. PATENT DOCUMENTS 4,193,196  3/1980  Kuris et al. ............................ 433/82
4,643,678  2/1987  Hansen ................................. 433/215

Primary Examiner—Robert Peshock
Attorney, Agent, or Firm—Charles J. Brown

[57] ABSTRACT

A method of cutting and lubricating human hard tissue during power tool cutting wherein the tissue subjected to cutting has directed against it a liquid admixture of water as a cooling agent, alcohol as an anti-infection agent and glycerin as a lubricant.

4 Claims, No Drawings

METHOD OF COOLING AND LUBRICATING HUMAN HARD TISSUE DURING POWER TOOL CUTTING

BACKGROUND OF THE INVENTION

Water has been commonly used as a coolant in dental drilling though, as described in my co-pending application entitled "Liquid Admixing Apparatus for Dental Water-Injection Systems", Ser. No. 752,300 filed July 5, 1985, the addition of flavoring agents or the like to coolant water has been proposed to provide a pleasant taste in the patient's mouth during and after the dental procedure. However, conventional use of water-based coolants does not prevent the formation of microscopic, but nonetheless observable, chipping, ridging and surface cracking of the tooth enamel and dentin from the action of the drill bur. It is the principal purpose of the present invention to improve upon water coolants used during the drilling or cutting of human hard tissue such as tooth enamel so that a cleaner, smoother surface topography results. It is a further and equally important purpose of the present invention to reduce substantially the drilling time required to cut or drill into tissue of a given hardness. All of this is to be achieved by a solution which acts as a coolant, a lubricant and an anti-infection agent and which includes separate components for each of those purposes.

SUMMARY OF THE INVENTION

A method of cooling and lubricating human hard tissue during power tool cutting is provided by the invention. It comprises the steps of first admixing about 25% to 70% by volume of water and about 5% to 35% by volume of potable alcohol and about 10% to 45% by volume of glycerin, followed by directing this admixture in a flow against the hard tissue subjected to cutting. In its preferred form the method concerns the cooling and lubricating of a human tooth during high-speed drilling, wherein the admixture is substantially 40% by volume of water with a flavoring agent added, substantially 20% by volume of ethanol and substantially 40% by volume of glycerin.

Glycerin, as the term is used herein, means the commercial grade containing glycerol in high concentration usually with a small amount of water, and suitable for human consumption.

DESCRIPTION OF PREFERRED EMBODIMENT

Apparatus for directing a flow of a liquid admixture against human hard tissue is described in my aforementioned copending patent application and can readily be employed in the practice of the present method during dental drilling procedures. Reference hereafter to human hard tissue, however, is intended to include tooth structures and any dental filling material embedded therein and also human bone tissue.

Various mixtures of different amounts of water as a coolant, glycerin as a lubricant and potable alcohol as an anti-infection agent were tested as described below. One of these is a commercially available mouthwash containing glycerin, alcohol and water. It was found that the duration of cutting or drilling for a given depth of cutting on a tooth of a given hardness could be significantly reduced by the presence of glycerin. It was also found from an electron microscope study of tooth enamel cut by the method of the invention that a cleaner, smoother surface topography was achieved.

These microscope studies were made on tooth enamel cut with both tungsten carbide and diamond burs. At higher magnifications tooth enamel cut with the solution called for in the method of the invention showed a much cleaner, less smeared and more uniform appearance without the degree of peaks and valleys, chipping or surface cracking seen on tooth enamel cut with only air and water applied in accordance with the prior art.

In the following tests a single tooth was mounted firmly on a small wheeled carriage which was pulled on a track by a constant force of 70 grams into a stationary-mounted high-speed dental handpiece operated at an air pressure of 30 psi. A new carbide bur was used in each of the tests reported below and the bur was permitted to penetrate 4 millimeters (or otherwise as noted) into the side of the tooth. The time required for such penetration was measured in each test as reported.

Various tests were carried out on different sample teeth, each of which had distinctive and individual hardness and drilling characteristics as is commonly recognized in dentistry. The first observation to be made is that in three of these tests the amount of glycerin added to the mixture was in the amount of 50% by volume, and in every case this proved to be excessive because it resulted in clogging of the high-speed handpiece. In each of the tests reported below where the glycerin was 40% or less, no such clogging occurred. Therefore it is reasonable to conclude that about 45% by volume of glycerin is a maximum for that component.

It became apparent in conducting many tests that the hardness of the sample teeth varied to such a degree that comparisons in each case had to be made between (a) water alone as in the prior art and (b) various compositions of water-alcohol-glycerin within the scope of the invention. The results of such tests, where water only was the control, are as follows:

|  | Seconds Cutting Time | Water-Alcohol-Glycerin Composition |
|---|---|---|
| Tooth No. 1 | 47.5 | 50-20-30 |
|  | 58.8 | 65-20-15 |
|  | 120 Max. | 100-0-0 |
| Tooth No. 2 | 42.0 | 40-20-40 |
|  | 56.0 | 52-18-30 |
|  | 120 Max. | 100-0-0 |
| Tooth No. 3 | 28.0 | 40-20-40 |
|  | 45.0 | 52-18-30 |
|  | 82.0 | 100-0-0 |
| Tooth No. 4 | 29.0 | 40-20-40 |
|  | 31.0 | 50-10-40 |
|  | 37.5 | 30-30-40 |
|  | 79.6 | 100-0-0 |

The composition 52-18-30 is the commercial mouthwash referred to previously.

It will be seen from these results that compositions containing from 30% to 65% water, from 10% to 30% alcohol and from 15% to 40% glycerin all performed well as compared to the all-water solution. It is reasonable to extend these parameters by approximately 5% so that it can be said that the improved cutting times are achievable by admixtures of about 25% to 70% by volume of water, 5% to 35% by volume of potable alcohol and 10% to 45% by volume of glycerin. For dental purposes the alcohol should, of course, be suitable for human consumption ethanol is preferred.

I claim:

1. A method of cooling and lubricating human hard tissue during power tool cutting thereof which comprises
    (a) admixing about 25% to 70% by volume of water and about 5% to 35% by volume of potable alcohol and about 10% to 45% by volume of glycerin, and
    (b) directing a flow of the admixture against the hard tissue subjected to cutting.

2. A method according to claim 1 wherein the hard tissue is a tooth, the cutting is high-speed drilling, and the admixture includes a flavoring agent in the water.

3. A method according to claim 1 wherein the alcohol is ethanol.

4. A method of cooling and lubricating a human tooth during high-speed drilling thereof which comprises
    (a) admixing substantially 40% by volume of water with a flavoring agent added and substantially 20% by volume of ethanol and substantially 40% by volume of glycerin and
    (b) directing a flow of the mixture against the tooth subjected to drilling.

* * * * *